US012697248B2

(12) United States Patent
Spuhler et al.

(10) Patent No.: US 12,697,248 B2
(45) Date of Patent: Aug. 4, 2026

(54) SYSTEM FOR SECURING A PATIENT SUITABLE FOR EYE SURGERY

(71) Applicants: CENTRE NATIONAL DE LA RECHERCHE SCIENTIFIQUE, Paris (FR); UNIVERSITE DE MONTPELLIER, Montpellier (FR); ACUSURGICAL, Montpellier (FR)

(72) Inventors: Christoph Spuhler, Montpellier (FR); Yassine Haddab, Montpellier (FR); Philippe Poignet, Gignac (FR); Antoine Morel, Montpellier (FR); Alonso Sanchez, Juvignac (FR); Nicolas Le Borgne, Montpellier (FR)

(73) Assignees: CENTRE NATIONAL DE LA RECHERCHE SCIENTIFIQUE, Paris (FR); UNIVERSITE DE MONTPELLIER, Montpellier (FR); ACUSURGICAL, Montpellier (FR)

( * ) Notice: Subject to any disclaimer, the term of this patent is extended or adjusted under 35 U.S.C. 154(b) by 324 days.

(21) Appl. No.: 18/037,280

(22) PCT Filed: Nov. 17, 2021

(86) PCT No.: PCT/EP2021/081965
§ 371 (c)(1),
(2) Date: May 16, 2023

(87) PCT Pub. No.: WO2022/106457
PCT Pub. Date: May 27, 2022

(65) Prior Publication Data
US 2023/0301826 A1 Sep. 28, 2023

(30) Foreign Application Priority Data
Nov. 17, 2020 (FR) .................................. FR2011777

(51) Int. Cl.
*A61F 9/00* (2006.01)
*A61B 34/00* (2016.01)
*A61B 90/20* (2016.01)

(52) U.S. Cl.
CPC ................ *A61F 9/00* (2013.01); *A61B 34/25* (2016.02); *A61B 90/20* (2016.02); *A61F 2009/0035* (2013.01)

(58) Field of Classification Search
CPC .... A61F 9/00; A61F 2009/0035; A61B 34/25; A61B 90/20
(Continued)

(56) References Cited

U.S. PATENT DOCUMENTS 5,752,950 A 5/1998 Frey et al.
6,544,193 B2 4/2003 Abreu
(Continued)

FOREIGN PATENT DOCUMENTS

EP 2 606 864 A1 6/2013
WO WO 01/80726 A2 11/2001
(Continued)

OTHER PUBLICATIONS

International Search Report and Written Opinion for corresponding PCT Application No. PCT/EP2021/081965, mailed Feb. 14, 2022, Machine Translation of Written Opinion (5 sheets).

*Primary Examiner* — Ahmed M Farah
(74) *Attorney, Agent, or Firm* — ArentFox Schiff LLP

(57) ABSTRACT

Disclosed is a system (100) for securing a patient, intended to interact with a robotic platform equipped with a surgical instrument (30) suitable for eye surgery, the system comprising: —at least one ocular sensor (110) capable of detecting movement of an eye (10) of the patient and/or at least one cephalic sensor (120) capable of detecting a movement of the head (20) of the patient; and —a data processing
(Continued)

means (130) for receiving data from the ocular sensor (110) and/or the cephalic sensor (120), processing the data in order to determine a level of risk for the patient on the basis of a predetermined criterion, then automatically sending a command for securing the patient to the robotic platform, the command being dependent on the previously determined risk level.

10 Claims, 4 Drawing Sheets

(58) Field of Classification Search
USPC ............................................................ 606/1
See application file for complete search history.

(56) References Cited

U.S. PATENT DOCUMENTS

| | | | |
|---|---|---|---|
| 11,759,359 B2 * | 9/2023 | Paudel ................... | A61F 9/008 |
| | | | 606/4 |
| 2009/0248036 A1 * | 10/2009 | Hoffman ............ | A61B 1/00149 |
| | | | 606/130 |
| 2015/0342695 A1 | 12/2015 | He et al. | |
| 2021/0038426 A1 | 2/2021 | Boularot et al. | |
| 2022/0079694 A1 * | 3/2022 | Freiin Von Kapri .. | A61B 34/37 |
| 2022/0249183 A1 * | 8/2022 | Charles ................. | A61B 34/25 |

FOREIGN PATENT DOCUMENTS

| WO | WO 02/064031 A2 | 8/2002 |
|---|---|---|
| WO | WO 2019/145487 A1 | 8/2019 |

* cited by examiner

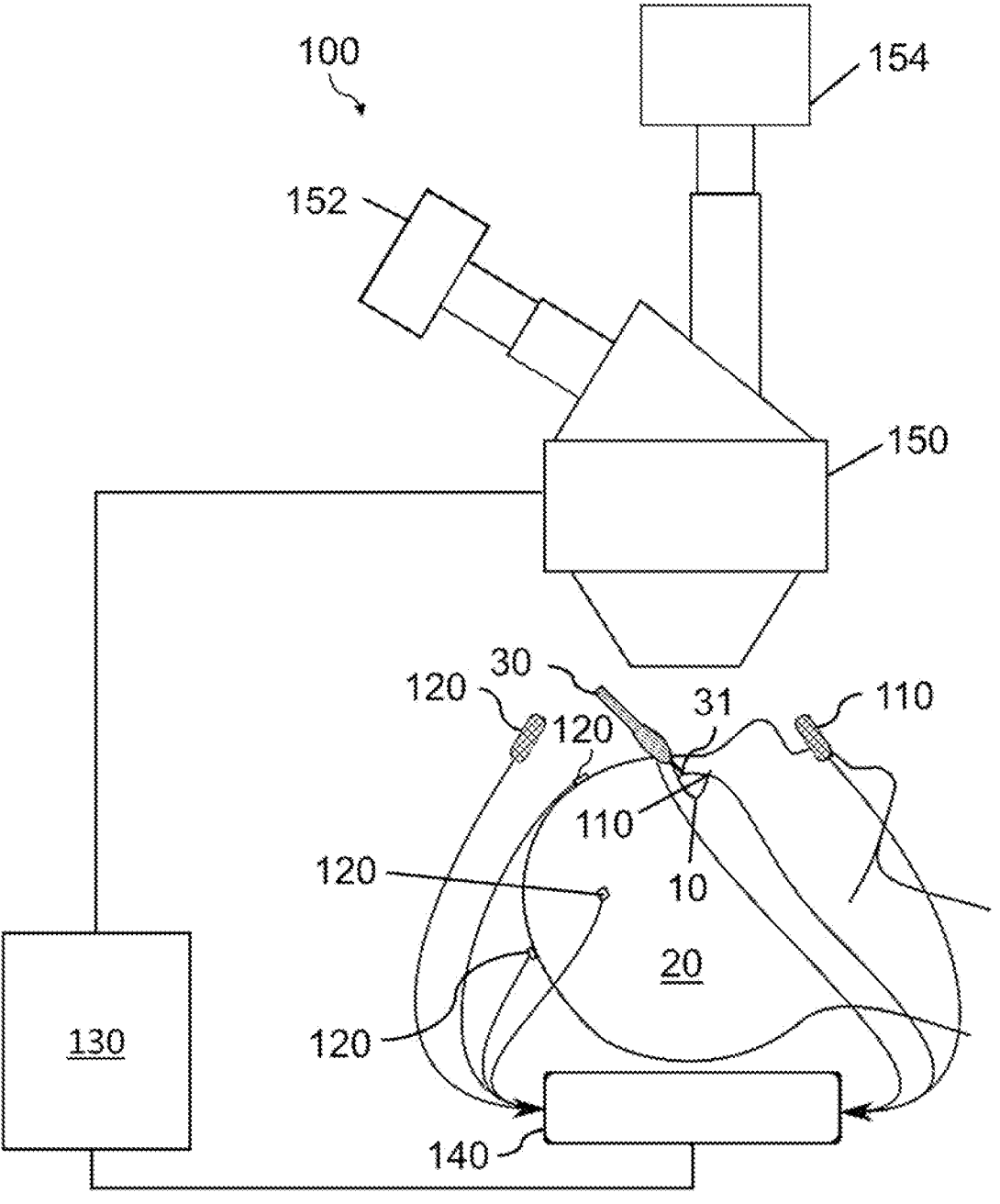
[Fig. 1]

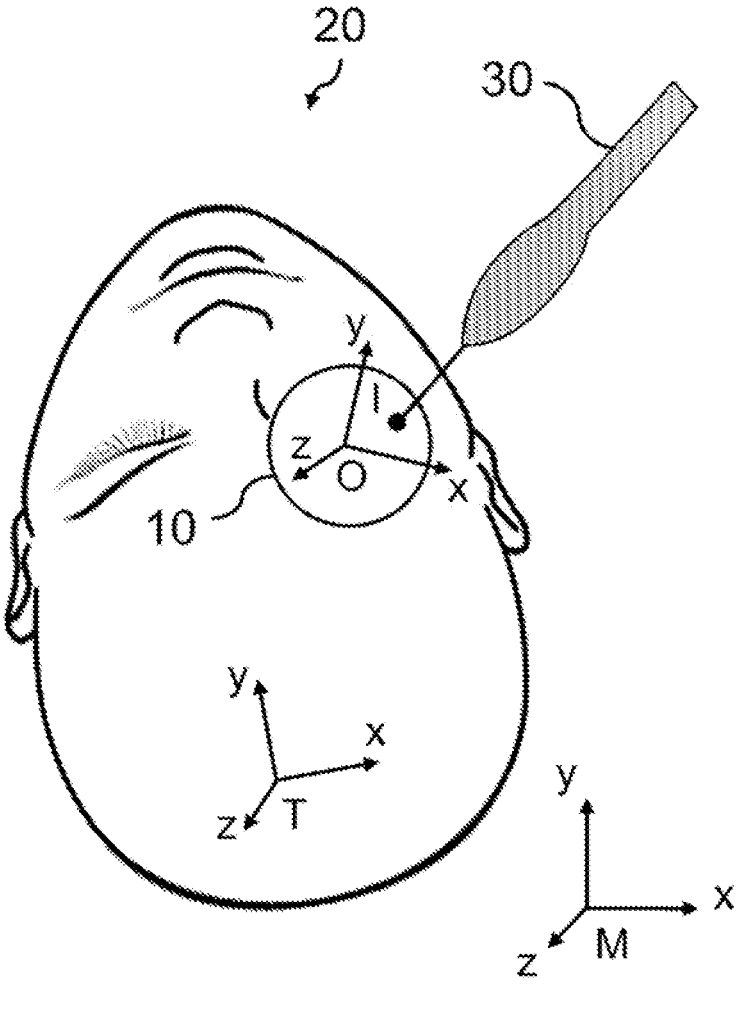
[Fig. 2]
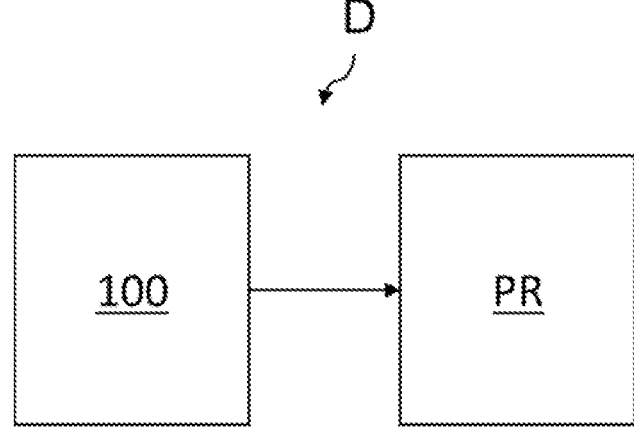
[Fig. 3]

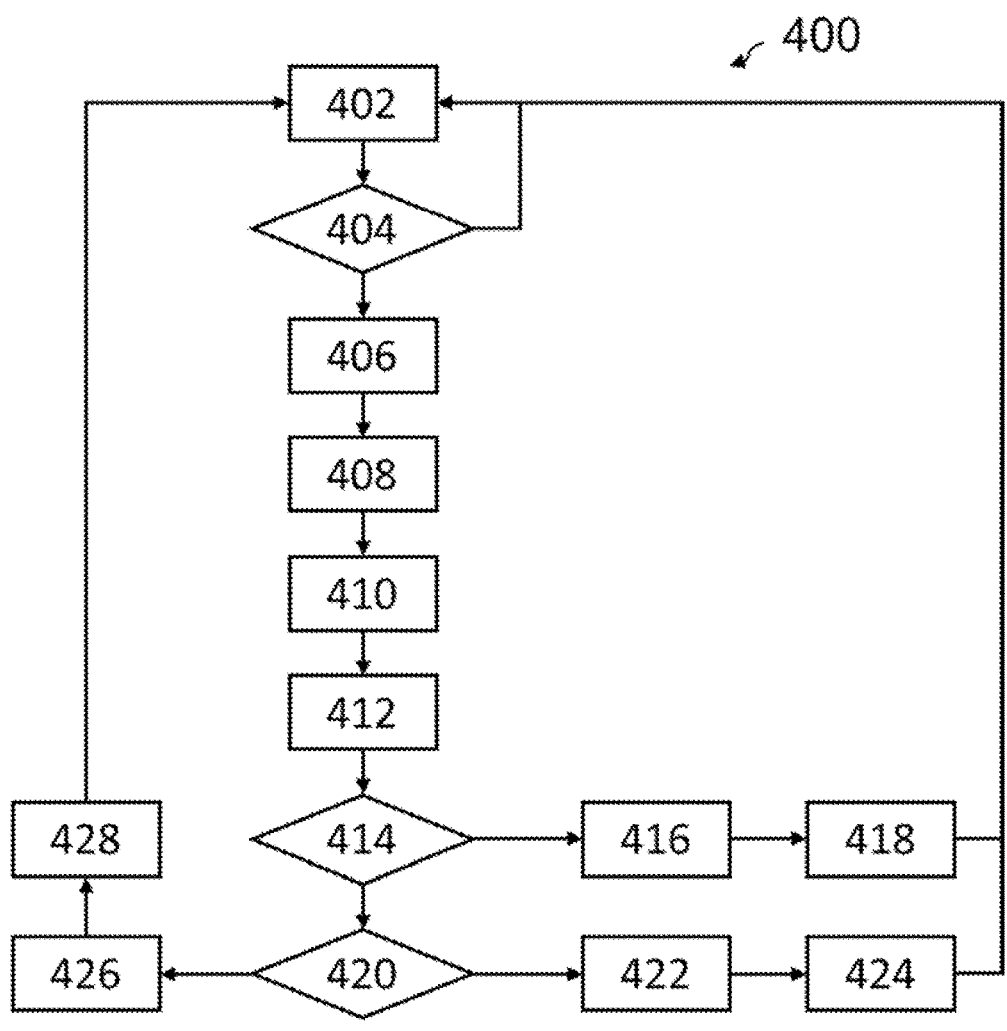
[Fig. 4]
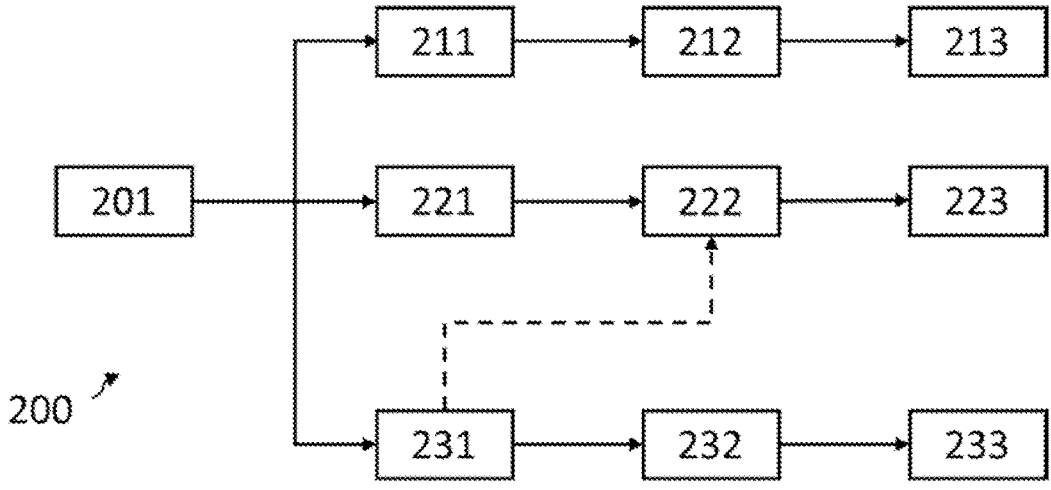
[Fig. 5]

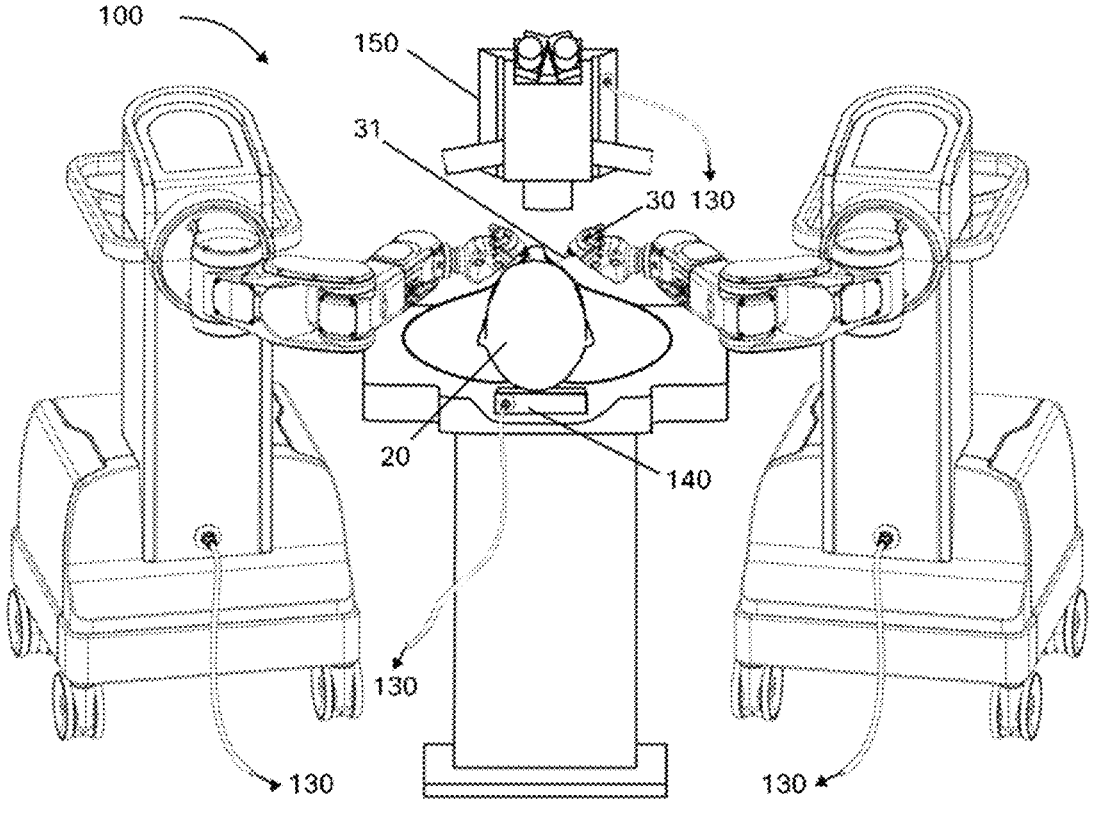
[Fig. 6]

SYSTEM FOR SECURING A PATIENT SUITABLE FOR EYE SURGERY

CROSS-REFERENCE TO RELATED APPLICATIONS

This application is a National Phase Patent Application and claims priority to and the benefit of International Patent Application No. PCT/EP2021/081965, filed on Nov. 17, 2021, which claims priority to and the benefit of French Patent Application No. FR2011777, filed on Nov. 17, 2020. The entire contents of both of which are incorporated herein by reference.

TECHNICAL FIELD OF THE INVENTION

The present invention relates to a securing system for securing a patient, intended to cooperate with a robotic platform and suitable for a vitreoretinal surgery, or eye surgery, a device comprising such a system and an associated method.

TECHNICAL BACKGROUND

The eye surgery is a delicate surgery that is performed by inserting instruments into the eye through a cannula referred to as trocar, which is placed on the anterior portion of the eye. This access allows us to pass through the vitreous and reach the posterior portion of the eye, where the retina is located, in order to carry out the surgical act.

Robots allowing to carry out this type of surgery exist. Their principle consists in letting the practitioner carry out the surgical gesture on a driving interface and then reproduce it on the instrument thanks to a robotic platform. These systems, referred to as remote manipulation systems, offer many advantages, for example by allowing the amplitude of the initial gesture to be increased or by filtering out the sudden movements and the tremors of the practitioner. However, they have a major disadvantage related to the potential for movement of the patient.

In most cases, the patient only receives a local anaesthesia to prevent the sensation and the movement of the eye. However, for a variety of reasons, they can still occur. In addition, a local anaesthesia does not prevent other movements, such as those of the head, from occurring. In other cases, it may also happen that the patient, even under general anaesthesia, wakes up and makes unexpected movements. These movements are a source of danger for the patient, as even a slight contact between the instrument and the eye, in particular the retina, is sufficient to cause irreversible damage, and a more serious collision can have even more serious consequences.

During a manual surgical act, the practitioner positions himself in such a way as to be able to perceive and accompany any movements of the patient with his hands. If necessary, the practitioner is able to react to make the patient safe from the surgical instrument. During a robotic surgical act, the direct contact between the practitioner and the patient is lost. The practitioner is then less sensitive to the possible movements of the patient. In addition, because the surgical instrument is rigidly carried by the robotic platform, it remains immobile even if it is subjected to a collision or an effort. The risk of serious injury becomes greater during a robotic surgery than during manual surgery and it is therefore essential to detect the movements of the patient in order to protect him or her from negative consequences.

The movements of the head of the patient can be mitigated by using an immobilisation mechanism, allowing to restrict the lateral movements of the head or that the patient raising the head, but this does not guarantee that the eye of the patient will not move at all.

Systems for detecting the movement of the eye can be used to monitor the progress of an operation as described in the documents U.S. Pat. No. 5,752,950, WO 01/80726 A2 or WO 02/064031 A2. However, these devices are designed to be used during a laser processing of the eye by deactivating the laser in case of movement of the eye.

This type of system does not allow to ensure the safety of the patient during a robotic operation. However, the management of the movements of the patient is a key issue for the success of a robotic surgery.

The existing robotic systems can incorporate a mechanism to rapidly move the instrument away from the eye of the patient, triggered by an action of the user. This type of manual triggering has several major disadvantages. The lack of direct contact between the patient and the practitioner prevents the latter from safely and quickly detecting the movements of the patient. In addition, the reaction time of the practitioner may be slower than the movement of the patient, not necessarily protecting from a risk of injury. Finally, the movement to safety is always the same and does not adapt to the situation. It may even unnecessarily disrupt the course of the surgical operation and in some cases may not be effective enough to prevent injury to the patient.

SUMMARY OF THE INVENTION

The present invention is intended to solve at least one of the above-mentioned disadvantages. In particular, the present invention aims to propose a securing system for securing a patient suitable for a surgery of the eye that is reliable and easy to implement.

To this end, the invention proposes a securing system for securing a patient, intended to cooperate with a robotic platform equipped with a surgical instrument adapted for a surgery of the eye, said system comprising:

at least one ocular sensor capable of detecting a movement of an eye of the patient and/or at least one cephalic sensor capable of detecting a movement of a head of the patient; and a data processing means configured to receive data from the ocular sensor and/or the cephalic sensor, process the data to determine a level of risk to the patient based on a predetermined criterion, and then automatically emit a securing command for securing the patient to the robotic platform, the securing command being dependent on the previously determined level of risk.

Thus, the invention ensures a reliable measurements due to the redundancy of the sensors that allow the detection of the movements to improve the safety of a patient. The measurements of head and/or eye movements can be compared and complemented in order to know precisely the nature of the movement and the possible consequences for the patient.

The system according to the invention may comprise one or more of the following characteristics, taken alone or in combination with each other:

the system comprises a surgical microscope configured to acquire at least one type of digital image of the retina of the eye and of a free end of the surgical instrument;

the type of digital image is a stereo-microscopic image and/or a sectional and depth image.

The invention also relates to a device comprising a system as described above and a robotic platform equipped with a surgical instrument suitable for the surgery of the eye.

The invention also relates to a method for securing a patient implemented with a device as described herein when the surgical instrument is outside the patient, the securing method comprising the following steps:

a) obtaining data relating to the movements of the eye and/or of the head of the patient;

b) processing the data obtained in step a) so as to determine a level of risk for the patient on the basis of at least one predetermined criterion;

c) automatically emitting a securing command for securing the patient, the securing command being dependent on the previously determined risk level;

d) receiving the securing command at the level of the robotic platform, which automatically causes the robotic platform to take a securing action for securing the patient.

The method according to the invention may comprise one or more of the following characteristics, taken alone or in combination with each other:

the data collected in step a) are selected from at least one measurement of position, effort, vibration and/or electro-physiological activity of the eye and/or of the head of the patient;

in step b), a geometric model is defined for the head and/or the eye of the patient so as to measure a distance and a relative velocity between a free end of the surgical instrument and the eye, the geometric model defining a time-to-impact criterion between said free end of the surgical instrument and the eye;

in step b), the risk level is determined by comparing the time-to-impact criterion with a reaction time, the reaction time being a sum of a reaction time of a practitioner and a reaction time of the robotic platform driven by the practitioner;

the securing action is an audible, visual and/or haptic warning;

the securing action is an audible, visual and/or haptic warning coupled with a movement of the surgical instrument away from the patient.

BRIEF DESCRIPTION OF THE FIGURES

Further characteristics and advantages of the invention will become apparent from the following detailed description, for the understanding of which reference is made to the attached drawings in which:

FIG. 1 is a schematic view of a securing system for securing the patient according to one embodiment;

FIG. 2 is a schematic view of a geometric model of the head and of the eye of the patient;

FIG. 3 is a very schematic representation of a device, according to one embodiment, comprising the system of FIG. 1;

FIG. 4 is a block diagram of a method for securing a patient implementing the device of FIG. 3; and FIG. 5 is a block diagram of a risk concept.

FIG. 6 is a diagram showing the robotic platform, the patient and the surgical instrument.

DETAILED DESCRIPTION OF THE INVENTION

In the following detailed description, we refer to an eye 10. This semantic usage is not limited only to the ocular globe and can be applied to any component of the ocular globe, such as for example the retina.

Reference is now made to FIG. 1 which illustrates one embodiment of a securing system 100 for securing a patient suitable for a surgery of the eye.

The securing system 100 is intended to cooperate with a robotic platform PR, not shown in FIG. 1, equipped with a surgical instrument 30. The securing system 100 comprises at least one ocular sensor 110 and/or at least one cephalic sensor 120 and a data processing means 130.

The ocular sensor 110 is adapted to detect a movement of an eye 10 of the patient. In addition, a direction, a rotation and/or an amplitude of the movement of the eye 10 relative to an initial state can be measured. This initial state corresponds to the state in which the eye 10 is in when the ocular sensor 110 is calibrated.

The ocular sensor 110 may be a position sensor, selected from an optical tracker sensor, a rangefinder or "time-of-flight" camera sensor or an electromagnetic tracker sensor.

The cephalic sensor 120 is adapted to detect a movement of a head 20 of the patient, which movement may be due to, among other things, an action of the neck or the nape of the patient. In addition, a direction, a rotation and/or an amplitude of the movement of the head 20 relative to an initial state can be measured. This initial state corresponds to the state of the head 20 during the calibration of the cephalic sensor 120.

The cephalic sensor 120 may be a position sensor, selected from a central inertial sensor, an optical tracker sensor, a rangefinder or "time-of-flight" camera sensor or an electromagnetic tracker sensor.

The sensors 110, 120 listed above, taken as a unit, are known to the person skilled in the art and meet the criteria of reliability, ease of installation, overall dimension, sterility and cost considered to be suitable for a surgery of the eye carry out via a robotic platform PR.

Note that a sensor may also be used to detect a movement of the robotic platform PR carrying the surgical instrument 30. However, the position of the platform PR is in principle already known via the internal sensors of its own actuators. As a result, the position of the instrument 30 is, in principle, also known.

Although not shown in FIG. 1, the detection of movements of the eye 10 and/or the head 20 of the patient may be accompanied by measurements of electro-physiological effort or activity such as muscular activity. The measurements of efforts at the level of the head 20 can be made by means of, for example, pressure sensors installed on elements immobilising the head 20 of the patient. In this way, it is possible to measure pressure variations related to the efforts exerted by the head 20 of the patient and which may cause a movement. The measurements of electro-physiological activity, such as muscular activity, particularly of the eye 10, can be carry out by means of electro-oculograms. In this way, it is possible to measure the activity of the muscles of the eye and thus be able to detect the movements, saccadic or voluntary, that may result.

In a preferred configuration at least one electromagnetic tracker is used as ocular sensor 110 and at least one electromagnetic tracker is used as cephalic sensor 120. It is understood that in this configuration at least two sensors 110, 120 are used, one of which is an ocular sensor 110 and the other a cephalic sensor 120. Unlike an optical tracker, an electromagnetic tracker is insensitive to the cloaking problems of the targets. In addition, it allows the simultaneous measurement of multiple points on multiple targets in a same spatial reference frame using a single electromagnetic field generator 140. This is an advantage in terms of space and installation time. It is further preferred to use a plurality of electromagnetic trackers, located at various points of interest on the head 20 and at the level of the eye 10, allowing to measure both the position of the head 20 and of the eye 10. This electromagnetic tracker can, for example, be an Aurora® system, marketed by Nothern Digital Inc.

Furthermore, a redundancy of the sensors 110, 120, i.e. the use of several ocular sensors 110 for a same measurement of the movement of the eye 10 and several cephalic sensors 120 for a same measurement of the movement of the head 20, allows to ensure the long-term data acquisition, e.g. during the surgical operation, by preventing the failure of a sensor 110, 120. Indeed, the probability that all the sensors 110, 120 are inoperative at the same time is much lower than the probability of the momentary failure of a single sensor 110, 120. In fact, the redundancy of the sensors 110, 120 improves the safety of the patient.

In the embodiment shown in FIG. 1, the securing system 100 comprises, in addition to the ocular and cephalic sensors 110, 120, an optical system of a surgical microscope 150. This type of apparatus is generally already present in an operating block and allows the generation of at least one type of digital image of the retina of the eye 10 and/or of the free end 31 of the instrument 30. The generated image may be a stereo-microscopic image, obtained via cameras 152, and/or a cross-sectional and depth view, obtained by optical coherence tomography (OCT) via a scanner OCT 154. This type of imaging allows the retina of the eye 10 and the free end 31 of the surgical instrument 30 to be visualised and information to be obtained about the distance between them.

The at least one ocular sensor 110 and/or the at least one cephalic sensor 120 are configured to exchange information in real time with a data processing means 130. The information exchanged is raw measurements of positions, efforts and/or muscle activity of the eye 10 and/or the head 20 of the patient.

The data processing means 130 is configured to receive the data of the raw measurements made from the at least one ocular sensor 110 and/or the at least one cephalic sensor 120 and, if present, from a surgical microscope 150. The means 130 is further adapted to be able to process this data to determine a level of risk to the patient based on a predetermined criterion, and then to be able to emit, automatically, a securing command for securing the patient to the robotic platform PR. It is understood that the securing command is dependent on the level of risk previously predetermined by a user.

The Applicant also proposes a device D, schematically illustrated in FIG. 3, comprising a securing system 100 as described above and a robotic platform PR equipped with a surgical instrument 30 adapted for the surgery of the eye 10.

The Applicant also proposes a method 400 for securing a patient implementing a device D, as defined above, when the surgical instrument 30 is outside the patient. The method comprises the following steps:

a) obtaining data relative on the movements of the eye 10 and/or the head 20 of the patient;

b) processing the data obtained in step a) so as to determine a level of risk for the patient on the basis of at least one predetermined criterion;

c) automatically emitting a securing command for securing the patient, the securing command being dependent on the previously determined risk level; and

d) receiving said securing command at the level of the robotic platform PR, this automatically causes the robotic platform PR to take a securing action for securing the patient.

This method 400 is detailed in the following and illustrated in FIG. 4. Step (a) comprises the sub-steps 402 to 408. In step a), the data relating to the movements of the eye 10 and/or of the head 20 are collected in a sub-step 408 by the data processing means 130. This data are obtained from measurements made by the at least one ocular sensor 110 and/or the at least one cephalic sensor 120 of the system 100 in sub-step 402. In case a sensor is placed at the level of the instrument, the data of the measurements made by this sensor can also be collected. The data from the measurements made by sensors internal to the robotic platform PR can also be collected. In case a surgical microscope 150 is coupled to the system 100, the data of the measurements obtained by the images are collected. All of these data evolve according to the different movements of the patient.

In a sub-step 404, the data processing means 130 interrogates the ocular sensor 110 and/or the cephalic sensor 120 for knowing the location of the eye 10 and/or of the head 20. In case of movement, the measurement data are transmitted to the data processing means 130. If there is no movement, the means 130 restarts the sub-step 402.

The data collected in sub-step 408 may be selected from at least one of position, effort, vibration, and/or electro-physiological activity measurements of the eye 10 and/or of the head 20.

In a preferred embodiment, the measurements made are positional measurements. These measurements allow to provide information on the relative position of at least one point of interest located on different bodies. These bodies may be the head 20 of the patient, an eye 10, i.e. the ocular globe or the retina, the free end 31 of the surgical instrument 30 or the robotic platform PR.

At the level of the head 20, at least one point of interest may be selected in an anatomical region with little tissue deformation during the movements of the patient. Thus, the coronal, parietal, occipital, superior frontal regions of the skull and/or the nasal bones are most suitable. This point of interest may also be located at the level of the surgical equipment that is secured to the head 20, such as the retractors for the eyes 10. At the level of the ocular globe, at least one point of interest may be selected on the sclera of the eye 10 or on a cannula used to insert the instrument 30 during surgery.

Many sensors 110, 120 exist to measure the position of these different points of interest and have already been described previously.

The measurement of the position of the head 20 is important because its movements are the most dangerous. Indeed, their amplitude is large, but they can occur especially in the axis of the instrument 30, i.e. upwards when the patient is lying down, and thus bring the free end 31 of the instrument 30 dangerously close to the eye 10.

The measurement of the position of the eye 10 can allow to complement the measurement obtained with a cephalic sensor 120, for example by confirming or denying a movement of the head 20 of the patient. It can also be used to demonstrate a rotation of the ocular globe alone in its orbit, for example if the patient changes the direction of his or her gaze. The placement of the at least one ocular sensor 110 may be complex, due to the limited space available on the eye 10, but the measurements of the position of the eye 10 are more advantageous than those of the position of the head 20.

The measurements carried out can be mixed, combining measurements of positions, efforts and/or electro-physiological activity. It is understood that with several types of measurement the diversification of the data collected is improved, allowing for better forecasting. In addition, a same type of measurement can be carried out by another sensor. It is understood that the redundancy of sensors of a same type allows to refine the predictions and to improve the reliability.

In addition, each measurement consists of a numerical value and an uncertainty on this value. This uncertainty depends on the physical principle the sensor uses to acquire its signal and the calculations it carries out to process it and derive the measurement.

In addition, the sensors 110, 120 may also provide measurements that are qualified as outliers due to, among other things, an obscuration, a light reflection or an electromagnetic interference. These aberrations can interfere with the calculations of the subsequent steps of the method 400. They are then filtered in a sub-step 406 before being collected in sub-step 408, and, if necessary, eliminated using an algorithm based on the verification of spatio-temporal coherence. In this way, two corrections are carried out after the processing means receives a raw measurement. The belonging of the raw measurement to a predefined interval is checked. This interval can be defined by the user and varies depending on the type of sensor 110, 120 used or the point of interest considered. If the raw measurement does not belong to this interval, the further it deviates from it, the greater the associated uncertainty. The variation over time of the raw measurement is also calculated. The more it exceeds a predefined rate, the greater the uncertainty associated with the raw measurement. A measurement with a high uncertainty will then have little impact on the calculation carried out in the next step.

In step a), measurements correlated to the movements of the patient are acquired in real time. These measurements are processed in step b) by the data processing means 130 in order to determine a risk level based on at least one predetermined criterion.

For example, we can identify a first criterion, referred to as "time-to-impact", which takes into account the concrete reason leading to an impact between the eye 10 of the patient and the instrument 30: faced with a movement of the patient, the practitioner has not had time to react. A second criterion, referred to as "intention to move", can, for example, take into account the initial reason that causes an impact between the eye and the instrument: the patient wanted to move.

Thus, in a sub-step 410, for each identified criterion, a simplified model allows to model the situation of the patient. Each model contains a limited number of degrees of freedom (DOF) which are determined by measurements. In other words, this step allows to interpret the measurements from the sensor or the sensors 110, 120 and allows to calculate the criteria used to estimate a risk level of the patient.

In the following we refer to the "time-to-impact" criterion described above. For the "time-to-impact" criterion, the distance and the relative velocity between the free end 31 of the instrument 30 and the eye 10 are measured. For this purpose, a geometric model, shown in FIG. 2, of the head 20 and the eye 10 of the patient is defined by assigning to the external environment, also referred to as world, a reference frame with centre M, to the head 20 a reference frame with centre T, to the eye 10 a reference frame with centre O and to the free end 31 of the instrument 30 a point I. The model considers the head 20 of the patient as a free solid in space, i.e. the transformation between the world reference frame M and the head reference frame T has six degrees of freedom. The model considers the eye 10 as a sphere in ball-and-socket connection with the head 20 through its orbit. The centre of this orbit is considered to be able to translate, slightly, into the head 20, which also gives six degrees of freedom to the transformation between the head reference frame T and the eye reference frame O. The tip of the instrument 30 is considered to be free, and therefore has three degrees of freedom. The model then comprises fifteen degrees of freedom.

When the system 100 is set up, a readjustment allows the initial transformations between the three reference frames M, T and O, as well as the diameter of the eye 10 to be known. As each patient is unique, this readjustment allows the positioning of the different reference frames to be calibrated and the system 100 to be adapted to each new patient and each new situation.

The movements of the patient will then cause these initial transformations between the reference frames M, T and O to evolve according to the fifteen degrees of freedom identified. For anatomical reasons, however, these latter are constrained in their amplitude compared to their initial value.

The position of the instrument 30 is, a priori, known because it is determined by the action of the surgeon on the robotic platform PR which holds the instrument 30. In other words, the position of the point I in reference frame M is known. However, in order to take all eventualities into account, an uncertainty can be attributed to the position of the point I.

The data processing step b) then consists of continuously determining the configuration of this model that best explains the acquired data. Several techniques can be used to achieve this. One of them proposes to solve an optimisation problem by methods such as Levenberg-Marquardt or Gauss-Newton. Such an optimisation problem has several advantages. Indeed, the initialization of the resolution algorithm can be done from the last estimated configuration. This is done at a high frequency, greater than at least 100 Hz to allow for fast system response, so the deviation from the current configuration is minimal, which will make the algorithm converge in very few iterations. Another advantage is that the stopping criterion of the algorithm can easily be given by the uncertainty of the measurements themselves.

Another resolution technique is based on a Kalman filtering. This method is a mathematical method known to the person skilled in the art and is suitable for estimating the state of a system. One of its advantages is that it directly indicates the precision with which this state is estimated, via a covariance matrix. The method consists of two phases. A first prediction phase aims to predict what the current state of the system should be based solely on its previous state. A second phase of updating the prediction takes place using the measurements performed during the first data acquisition step to provide the configuration that best explains the measurements, as well as the covariance matrix from which an uncertainty can be assessed.

Once the configuration of the model has been determined, the position of the point I in the reference frame O of the eye can be calculated, as well as its velocity (based on its previous position). The value of the "time-to-impact" criterion can thus be deduced.

Other criteria may be used to complete the estimation of the risk level of the patient and may require other models to be implemented. For example, the criterion "intention to move" can be considered to take into account measures of electro-physiological activity.

In the case where sensors of a different type are used, for example an effort sensor, models are needed to interpret the measurements and feed the geometric model. A Kelvin-Boltzmann model can be considered.

In general, during a manual surgery of the eye 10, the practitioner intuitively estimates the level of risk associated with the perceived movements. He then adapts his reaction. The greater the perceived risk for the patient, the greater the response of the practitioner.

In order to reproduce this estimation of the risk level, a concept 200 introduced by the ISO 14971 standard for risk management in the medical devices is used and illustrated in FIG. 5. The generic notions of dangerous situation 201, dangerous event 211, 221, 231 and damage 212, 222, 232 can be defined as follows: a dangerous situation 201 is a situation in which the patient is exposed to a dangerous event 211, 221, 231, e.g. when the patient moves the head 20 or the eye 10; a dangerous event 211, 221, 231 is a source of damage 212, 222, 232, e.g. if the instrument impacts the eye 10 or if the robotic platform PR hits the patient; a damage 212, 222, 232 is a physical injury of the patient. Furthermore, a damage 212, 222, 232 is characterised by a probability of occurrence, i.e. the probability that the conditions for the dangerous phenomenon or phenomena 211, 221, 231 causing it are met, and by a severity, i.e. the severity of the consequences of the damage 212, 222, 232.

The notion of risk 213, 223, 233 is defined and quantified by the combination of these quantities. During a dangerous situation 201, it can thus be noted that the more likely it is that a dangerous phenomenon 211, 221, 231 will occur and the more serious the damage 212, 222, 232 it may cause, the greater the risk 213, 223, 233 is considered to be. It should be noted that a dangerous situation 201 can lead to different dangerous events 211, 221, 231 and that a same dangerous event 211, 221, 231 can lead to different damage 212, 222, 232. It should also be noted that a damage 212, 222, 232 can be the consequence of different dangerous phenomena 211, 221, 231.

It is considered that whatever the damage or the damages 212, 222, 232 are considered, their severity is invariably significant, so that their level of risk 213, 223, 233 is proportional to the probability of their dangerous phenomenon 211, 221, 231 occurring.

In order to illustrate the general method, reference is made in the following, as an example, to the "time-to-impact" criterion, noted $\Delta T_{impact}$, allowing the probability of an instrument/eye impact to be estimated 30/10. It is considered infinite if there is no relative movement between the instrument 30 and the eye 10, or if the instrument 30 moves away from the eye 10. It decreases as soon as the movement of the eye 10 and/or the movement of the instrument 30 tends to bring them closer together. The time-to-impact is defined as the distance between the eye 10 and the instrument 30 divided by the relative velocity between the two.

A reaction time, denoted $\Delta T_{reaction}$, is defined as the sum of the reaction time of the practitioner and the reaction time of the robotic platform PR. The reaction time of the practitioner is considered to be the time between the moment the patient starts to move and the moment the practitioner starts to act on the driving interface of the robotic platform PR. The reaction time of the robotic platform PR is considered to be the time between the moment when its driving interface is stimulated and the moment when, in response, its actuators start to move. Both times are easily measured and can subsequently be considered constant and reproducible from one situation to another.

In a sub-step 412, the data processing means 130 compares the time-to-impact $\Delta T_{impact}$ with the reaction time $\Delta T_{reaction}$ so as to determine, in a sub-step 414, 420, a risk level that falls within a user-defined risk scale according to predefined conditions. Each of these conditions has a corresponding level of risk. An example of conditions predefined by the user is given in Table 1.

| Condition | Risk |
|---|---|
| $\Delta T_{impact} < \Delta T_{reaction}$ | Very high |
| $\Delta T_{reaction} \leq \Delta T_{impact} < 2\Delta T_{reaction}$ | High |
| $2\Delta T_{reaction} \leq \Delta T_{impact} < 3\Delta T_{reaction}$ | Moderate |
| $\Delta T_{impact} \geq 3\Delta T_{reaction}$ | Low |

As a non-limiting example, a practitioner with only a visual feedback from the patient has a reaction time of about 400 ms, while the robotic platform PR has a reaction time of about 100 ms, i.e. $\Delta T_{reaction}$ equal to 500 ms.

Typically, in sub-step 414, the criterion is compared to a first predefined condition. If it fulfils this first condition, it can be assigned a first risk level at a sub-step 416. In case the first condition is not met, the criterion is compared to a second predefined condition in a sub-step 420. If it meets this second condition, it may be assigned a second risk level at a sub-step 422 and so on until a nth condition corresponding to a negligible risk level is reached at sub-step 426.

Other criteria can be added to the previous one, such as the "intention to move" criterion already mentioned. This criterion can be directly related to the electro-physiological activity of the patient and it is the degree of activity that determines the level of risk.

If several criteria are used in parallel, they are combined to estimate the final risk level of the patient. This can take a simple form: the final risk is the highest risk of all those assessed. This can also take a complex form: the raw values of each criterion (time-to-impact, intention to move, etc.) can be fed into a Bayesian estimator or a neural network allowing to determine the final estimation of the risk of the patient.

For each risk level determined in sub-step 414, 420, an action is associated. In other words, for each condition predefined by the user, an action is planned in response. In a step c), the data processing means 130 automatically emits a securing command for securing the patient.

In a step d), the robotic platform PR receives the securing command emitted in step c), which automatically causes the robotic platform PR to take a securing action so that it provides an appropriate and graduated response according to the received securing command. Graduated response or graduated reaction means an action that is part of a series of actions that follow each other as the situation develops.

Generally, in a sub-step 416, 422, 426, the data processing means 130 concludes a risk level. It is understood that the first risk level of sub-step 416 is more important than the second risk level of sub-step 422, which is more important than the nth risk level of sub-step 426. At the end of sub-step 416, a first action is controlled by the means 130 on the robotic platform PR in a sub-step 418. At the end of sub-step 418, the securing action has been completed and the situation has returned to normal, the method 400 resumes at sub-step 402. After sub-step 422, a second action is controlled by the means 130 on the robotic platform PR in a sub-step 424. At the end of sub-step 424, the securing action has been completed and the situation has returned to normal, the method 400 resumes at sub-step 402. The nth level of risk, identified in sub-step 426, is the lowest of all and the action taken by the means 130 in a sub-step 428 is zero. At the end of sub-step 428, the method 400 resumes at sub-step 402.

Several actions for securing the patient can be ordered by the data processing means 130 depending on the level of risk.

A first group of actions may be caused in step d) when the instrument 30 is outside the patient, in the vicinity of the eye. It should be noted that the position of the instrument outside the eye of the patient may be its initial position before the start of surgical operation or it may be the result of the instrument being removed from the eye when the surgery is completed. It should also be noted that steps a) to d) can be carried out, in this case, when the instrument 30 is outside the patient.

The data processing means 130 of the system 100 may conclude that the level of risk is negligible, the situation is equivalent to a normal situation, and leaves the controls of the robotic platform PR to the practitioner. In other words, there is a non-intervention of the means 130.

The data processing means 130 may conclude that the risk level is low. It controls the emission of an alert via a warning means to alert the practitioner that the patient is moving or is likely to move. This warning may be visual, such as a flashing light or a display on a screen, and/or audible, such as a beep. The warning can also be haptic, i.e. by touch, for example with vibrations on the driving interface or in the pedals of the robotic platform PR. The means of warning is not exclusive and may be a combination of several means.

For any risk level equal to or higher than the low risk level, the warning action is automatically triggered. For any risk level above the low risk level, the data processing means 130 automatically overrides the practitioner to control the robotic platform PR. In other words, the positioning instructions are given directly by the data processing means 130.

The data processing means 130 may conclude that a level of risk is very high. It controls the spacing of the instrument 30 in order to prevent an impact with the patient, in particular an impact with the eye 10 of the patient. This allows sufficient space for the patient to move or for the practitioner to intervene without being hindered. In such a case, the movement initiated by the robotic platform PR is fast, for example 5 ms. The movement is also designed to avoid a collision with the patient or with another element in the operating block.

The invention described above has the advantage of providing a graduated action according to the situation at a given moment. Indeed, the sensor or the sensors 110, 120 allow to detect the movements, which may be more or less important, of the eye 10 and/or of the head 20 of the patient. The measurements made by the sensor or the sensors 110, 120 are processed and interpreted by the data processing means 130 which concludes on the action to be taken. This allows to ensure firstly that the patient is safe when moving and secondly that this is achieved without compromising the smoothness and speed of the surgical intervention.

In a particular situation, a second group of actions may be caused in step d) when the surgical instrument 130 is in the eye 10 of the patient, for example in contact with the retina. It should be noted that steps a) to d) can be carried out, in this case, while the instrument 30 is in the eye 10.

The data processing means 130 of the system 100 may conclude that the level of risk is negligible or low and take the same actions as for the first group identified above.

The data processing means 130 may conclude that there is a moderate level of risk, the surgical instrument 30 is away from the retina. By this reaction, the instrument 30 is kept away from the retina but remains in the eye 10, which allows a quick resumption of the surgical operation when the situation returns to normal. In such a case, the movement initiated by the robotic platform PR is fast, of the order of 5 ms for example, and takes place in the axis of the instrument. The movement away is also sufficiently accelerated and rapid to avoid a contact with the retina.

The data processing means 130 may conclude that a high level of risk exists and control the removal of the surgical instrument 30 from the eye 10. By this reaction, the instrument is completely removed from the eye but remains in close proximity so that it can be easily re-inserted, facilitating the resumption of the operation when the situation returns to normal. In such a case, the movement initiated by the robotic platform PR is fast, of the order of 5 ms for example, and allows the passage of the instrument through the centre of the trocar without exerting strong constraints on it, so as not to damage the sclera for example. The movement is also designed to avoid a collision with the patient or with another element in the operating block. This reaction may occur as a result of the instrument being moved away from the retina when the risk level is moderate. It is understood that the response to a high level of risk may include those implemented at lower levels of risk.

In an extreme case where the level of risk increases in real time, from the lowest to the highest, during an eye 10 operation, all actions can be applied in succession. The overall reaction can be broken down as follows: a warning is triggered and remains active to alert the practitioner, the control of the robotic platform PR is automatically subordinated to the data processing means 130 which orders the instrument 30 to be moved away from the retina and then removed from the eye 10 before being completely removed from the patient.

Under these conditions, it is understood that a method as follows can also be implemented with the device D, either with the surgical instrument 30 outside the patient or in the eye 10 of the patient:

A) obtaining data relative on the movements of the eye 10 and/or the head 20 of the patient;

B) processing the data obtained in step a) so as to determine a level of risk for the patient on the basis of at least one predetermined criterion;

C) automatically emitting a securing command for securing the patient, the securing command being dependent on the previously determined risk level; and D) receiving said securing command at the level of the robotic platform PR, this automatically causes the robotic platform PR to take a securing action for securing the patient.

It is then understood that the data collected in step A) may be selected from at least one of position, efforts, vibrations and/or electro-physiological activity measurements of the eye 10 and/or of the head 20 of the patient.

It is also understood that in step B), a geometric model may be defined for the head 20 and/or the eye 10 of the patient so as to measure a distance and a relative velocity between a free end 31 of the surgical instrument 30 and the eye 10. The geometric model allowing for defining a time-to-impact criterion between the free end 31 of the surgical instrument 30 and the eye 10.

It is further understood that in step B), the level of risk can be determined by comparing the time-to-impact criterion with a reaction time, defined as a sum of a reaction time of a practitioner and a reaction time of the robotic platform PR driven by the practitioner.

It is also understood that the action caused in step D) may be an audible, visual and/or haptic warning.

When the instrument is in the eye, the action caused in step D) may also be an audible, visual and/or haptic warning coupled with moving the free end 31 of the instrument 30 away from the retina of the eye 10, the instrument 30 then remaining in the eye 10.

When the instrument is in the eye, the action caused in step D) may also be an audible, visual and/or haptic warning coupled with a complete removal of the surgical instrument 30 from the eye 10.

When the instrument is in the eye, the action caused in step D) may also be an audible, visual and/or haptic warning coupled with a movement of the surgical instrument 30 away from the patient, and therefore from the eye.

The invention claimed is:

1. A securing system for securing a patient, intended to cooperate with a robotic platform equipped with a surgical instrument suitable for an eye surgery, said system comprising:

at least one ocular sensor capable of detecting a movement of an eye of the patient and/or at least one cephalic sensor capable of detecting a movement of a head of the patient; and a data processing means configured to receive data from said ocular sensor and/or said cephalic sensor, to process said data to determine a level of risk for the patient based on a predetermined criterion, and then emit, automatically, a securing command for securing the patient to said robotic platform, said securing command being dependent on the previously determined level of risk, wherein the level of risk is determined by defining a geometric model of the patient's head and/or eye to calculate a time-to-impact criterion between the surgical instrument and the eye, and comparing said time-to-impact criterion with a predetermined reaction time.

2. The system according to claim 1, further comprising a surgical microscope configured to acquire at least one type of digital image of the retina of the eye and of a free end of the surgical instrument.

3. The system according to claim 2, wherein the type of digital image is a stereo-microscopic image and/or a sectional and depth image.

4. A device comprising a securing system for securing a patient, and a robotic platform equipped with a surgical instrument adapted for eye surgery, wherein said system comprises:

at least one ocular sensor capable of detecting a movement of an eye of the patient and/or at least one cephalic sensor capable of detecting a movement of a head of the patient; and a data processing means configured to receive data from said ocular sensor and/or said cephalic sensor, to process said data to determine a level of risk for the patient based on a predetermined criterion, and then emit, automatically, a securing command for securing the patient to said robotic platform, said securing command being dependent on the previously determined level of risk, wherein the level of risk is determined by defining a geometric model of the patient's head and/or eye to calculate a time-to-impact criterion between the surgical instrument and the eye, and comparing said time-to-impact criterion with a predetermined reaction time.

5. A method for securing a patient implemented with a device according to claim 4 when the surgical instrument is outside the patient, said method comprising the following steps:

a) obtaining data relating on the movements of the eye and/or of the head of the patient;

b) processing the data obtained in step a) so as to determine a level of risk for the patient on the basis of at least one predetermined criterion;

c) automatically emitting a securing command for securing the patient, said securing command being dependent on the previously determined risk level;

d) receiving said securing command at the level of the robotic platform, this automatically causes the robotic platform to take a securing action for securing the patient.

6. The method according to claim 5, wherein the data collected in step a) are selected from at least one of position, effort, vibration and/or electro-physiological activity measurements of the eye and/or of the head of the patient.

7. The method according to claim 5, wherein in step b), a geometric model is defined for the head and/or the eye of the patient so as to measure a distance and a relative velocity between a free end of the surgical instrument and the eye, said geometric model defining a time-to-impact criterion between said free end of the surgical instrument and said eye.

8. The method according to claim 7, wherein, in step b), the risk level is determined by comparing the time-to-impact criterion with a reaction time, said reaction time being a sum of a reaction time of a practitioner and a reaction time of the robotic platform driven by said practitioner.

9. The method according to claim 5, wherein the securing action is an audible, visual and/or haptic warning.

10. The method according to claim 5, wherein the securing action is an audible, visual and/or haptic warning coupled with a movement of the surgical instrument away from the patient.

* * * * *